(12) United States Patent
Cajan et al.

(10) Patent No.: US 9,757,321 B2
(45) Date of Patent: Sep. 12, 2017

(54) HAIR STYLING COMPOSITION

(71) Applicant: KAO GERMANY GMBH, Darmstadt (DE)

(72) Inventors: Christine Cajan, Bad Ems (DE); Jutta Klutzny, Darmstadt (DE); Ina Brautigam, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 77 days.

(21) Appl. No.: 14/887,813

(22) Filed: Oct. 20, 2015

(65) Prior Publication Data
US 2016/0038398 A1 Feb. 11, 2016

Related U.S. Application Data

(63) Continuation of application No. 11/953,233, filed on Dec. 10, 2007, now abandoned.

(30) Foreign Application Priority Data

Dec. 13, 2006 (EP) .................................. 06025788

(51) Int. Cl.
| | | |
|---|---|---|
| A61Q 5/06 | (2006.01) | |
| A61K 8/73 | (2006.01) | |
| A61K 8/04 | (2006.01) | |
| A45D 7/04 | (2006.01) | |
| A61K 8/81 | (2006.01) | |
| A61K 8/92 | (2006.01) | |

(52) U.S. Cl.
CPC ............... *A61K 8/732* (2013.01); *A45D 7/04* (2013.01); *A61K 8/046* (2013.01); *A61K 8/8158* (2013.01); *A61K 8/8182* (2013.01); *A61K 8/92* (2013.01); *A61Q 5/06* (2013.01); *A61K 2800/22* (2013.01); *A61K 2800/43* (2013.01); *A61K 2800/54* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 3,373,126 A | 3/1968 | Lehrman | |
| 3,929,986 A | 12/1975 | Bouillon et al. | |
| 4,023,978 A | 5/1977 | Messina | |
| 4,450,151 A | 5/1984 | Shinozawa | |
| 4,761,273 A | 8/1988 | Grollier et al. | |
| 4,981,677 A | 1/1991 | Thau | |
| 5,009,880 A | 4/1991 | Grollier et al. | |
| 5,082,652 A | 1/1992 | Mayfield et al. | |
| 6,290,932 B2 | 9/2001 | Pratley | |
| 6,344,183 B2 | 2/2002 | Paul et al. | |
| 6,582,679 B2 | 6/2003 | Stein et al. | |
| 2001/0022967 A1* | 9/2001 | Brandt ..................... A61K 8/60 424/70.13 |
| 2001/0043912 A1 | 11/2001 | Michael | |
| 2003/0175229 A1 | 9/2003 | Giroud | |
| 2005/0002872 A1 | 1/2005 | Katz | |

FOREIGN PATENT DOCUMENTS

| | | |
|---|---|---|
| DE | 2521960 A1 | 4/1976 |
| DE | 2811010 A1 | 9/1978 |
| DE | 3044738 A1 | 6/1981 |
| DE | 3217059 A1 | 11/1982 |
| EP | 0337354 A1 | 4/1988 |
| EP | 0524612 A2 | 1/1993 |
| EP | 0640643 A2 | 3/1995 |
| EP | 0948958 A2 | 10/1999 |
| EP | 1598046 A1 | 11/2005 |
| GB | 1285547 | 8/1970 |
| GB | 1513672 | 5/1975 |
| JP | 2001226258 A | 8/2001 |

* cited by examiner

*Primary Examiner* — Jyothsna Venkat
(74) *Attorney, Agent, or Firm* — Norris McLaughlin & Marcus P.A.

(57) ABSTRACT

The present invention is related to a hair styling composition and process for styling keratin fibers, especially for hair. The object of the present invention is an aerosol composition for keratin fibers, especially for hair, based on an aqueous, aqueous-alcoholic or alcoholic medium comprising at least one natural starch and at least one propellant. Compositions according to present invention can furthermore comprise at least one film forming polymer, one or more surfactant, UV filter and direct hair dye.

14 Claims, No Drawings

HAIR STYLING COMPOSITION

This is a continuation patent application of U.S. Ser. No. 11/953,233 which was filed on Dec. 10, 2007, which claims foreign priority benefit under 35 U.S.C. §119 of European Application No. 06 025 788.8 filed Dec. 13, 2006.

The present invention is related to an aerosol hair styling composition for keratin fibres especially for hair.

Aerosol hair styling compositions have been widely used either as a spray or as a foam. In principal they comprise hair fixing polymers in an aqueous or aqueous alcoholic medium together with a propellant. Many fixing polymers have been suggested in the literature either synthetic or natural origin. Natural polymers so far suggested do not satisfy the expectations of consumers in terms of hair feel and hold of hair style for a long time and, therefore, overwhelmingly synthetic polymers are used.

The present inventors have surprisingly found out that an aerosol composition comprising natural starch in an aqueous, aqueous-alcoholic or alcoholic medium has excellent hair styling and restyling benefits together with excellent volumizing and bodifying effects. The hair feels natural upon touching and looks mattified.

Thus, the object of the present invention is an aerosol composition for keratin fibres especially for hair based on an aqueous, aqueous-alcoholic or alcoholic medium comprising at least one natural starch and at least one propellant.

Another object of the present invention is the use of an aerosol composition based on an aqueous, aqueous-alcoholic or alcoholic medium comprising at least one natural starch and at least one propellant for styling and restyling keratin fibres especially hair.

Still another subject of the present invention is a process for styling keratin fibres especially hair wherein an aerosol composition based on an aqueous, aqueous-alcoholic or alcoholic medium comprising at least one natural starch and at least propellant is applied onto wet and/or dry hair and hair is styled without rinsing off the composition.

With the term styling it is meant that the hair is freshly styled. With the term restyling it is meant that hair is already styled with an aqueous, aqueous-alcoholic or alcoholic composition of the present invention and after lapse of certain period of time a new style is given without using further composition of the present invention.

Thus, further object of the present invention is a process for restyling hair wherein keratin fibres especially hair already styled with an aerosol composition based on an aqueous, aqueous-alcoholic or alcoholic medium comprising at least one natural starch and at least propellant is with or without wetting a new style is given.

Compositions of the present invention comprise at least one natural starch at a concentration of 0.1 to 25%, preferably 1.5 to 20%, more preferably 2.5 to 15 and most preferably 4 to 15% by weight calculated to total composition excluding propellant. Within the meaning of the present invention any natural starch is suitable. Preferred are wheat, rice, potato, corn starches. Most preferred is rice starch.

Compositions of the present invention comprises at least one propellant at a concentration of 5 to 60%, preferably 5 to 50% more preferably 10 to 50% by weight calculated to total composition. Suitable propellants are lower alkanes such as n-butane, i-butane, propane, butane or their mixtures, as well as dimethylether (DME) either alone or in mixture with lower alkanes. Further suitable propellants are fluorinated hydrocarbons such as 1,1-difluoro ethane or tetrafluoroethane or their mixtures with each other, carbon dioxide and nitrogen or their mixtures with the above mentioned propellants. Preferred are lower alkanes such as propane, butane, n-butane, i-butane, and their mixtures and their mixture with DME at a alkane to DME weight ratio 10:1 to 1:10.

In a preferred form of the present invention, the compositions comprise at least one film forming polymer selected from the anionic, non-ionic, cationic and/or amphoteric or zwitterionic ones.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64, Plus from BASF AG and advantage LS-E from ISP.

Natural non-ionic polymers are as well suitable for the composition of the present invention. Those are such as cellulose, chitosan, guar gum, neutralised shellac and their derivatives.

As amphoteric polymers which can be used alone or in mixture with at least one additional nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl meth-acrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl(meth)acrylates or mono- or dialkyl aminoalkyl(meth)-acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Suitable anionic polymers alone or in combination with non-ionic polymers are vinyl-alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof of the type "Reten®"; etc.

Further suitable anionic polymers are Acrylate copolymers available under trade name Salcare SC 81, PEG/PPG 25/25 dimethicone/acrylate copolymer available under trade name Luviglex Silk from BASF, Acrylates/t-butylacrylamide copolymer available under trade name Ultrahold Strong, Advantage LC-E which is vinylcaprolactam/PVP/dimethyl-aminoethylmethacrylate copolymer and VA/crotonates copolymer available under trade name Luviset CA 66.

Composition of the present invention can comprise cationic polymers alone or in combination with non-ionic polymer. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643. Among these especially preferred is the compound know with the INCI name Polysilicone-9.

Concentration of polymers of anionic, cationic, non-ionic and/or amphoteric or zwitterionic character is in the range of 0.1-20%, preferably 0.5-15% and more preferably 1-12% and most preferably 2-10% by weight, calculated to the total composition excluding propellant.

In further preferred embodiment of the present invention, the compositions comprise at least one synthetic or natural oil. In principal, any oil allowed for cosmetic use is suitable for the compositions of the present invention.

Oils are those of synthetic and of natural ones. Natural oils are in principal any triglyceride suitable for cosmetic use. Non-limiting examples are avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention, It should as well be noted that compositions of the present invention can contain mixture of one or more natural oils and mineral oil.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

Synthetic ones are those of silicone oils. Here again any silicone oil either volatile and/or non-volatile is suitable for the compositions of the present invention. Preferred silicone oils are non-volatile silicone oils known with their INCI name as dimethicone, dimethiconol, and phenyltrimethicone which is an arylated silicone oil. Volatile silicone oils such as cyclomethicones may be used in combination with non-volatile silicones and/or other wax and/or oils mentioned above. Commercially, they are available from various companies for example Dow Corning with the known DC series, Wacker Chemie and Toray silicones. All commercially available non volatile silicones are suitable in the compositions of the present invention. Examples to those are DC 200 series, DC 556, DC 1401, DC 1403, DC 1501 and DC 1503.

Concentration of one or more oil in the compositions of the present invention is between 0.1 and 40%, preferably 0.25 and 35% more preferably 0.5 and 35% and most preferably 1 and 30% by weight calculated to total composition excluding propellant.

Compositions of the present invention may also comprise wax. Suitable and preferred examples are petrolatum, ozokerit, carnauba wax, paraffin, lanolin wax, candelila wax, bees wax, microcrystalline wax and cocoglycerides. Concentration of wax may be in the range of 0.01 to 20%, preferably 0.05 to 10% by weight calculated to total composition excluding propellant.

Compositions of the present invention may comprise one or more surfactant for solubilizing of one or more ingredients not soluble in the medium used or especially for the foam aerosol composition for achieving required foam especially the styling polymer when present does not have such properties. Suitable ones are of anionic, non-ionic, amphoteric and cationic surfactants or their mixtures.

As a rule any cationic surfactant is suitable for the compositions of the present invention. Preferably at least one cationic surfactant is selected from the compounds with the general formula

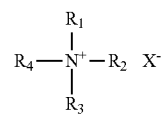

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and
and $R_2$, $R_3$ and $R_4$ are independent from each other H or lower alkyl chain with 1 to 4 carbon atoms or ethoxy or propoxy group with number of ethoxy or propoxy groups varying in the range of 0 to 4, and X is chloride, bromide or methosulfate.

Non-limiting examples to suitable cationic surfactants are cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, stearamidopropyldimethylamoonium chloride.

Suitable non-ionic surfactants are alkyl polyglucosides of the general formula

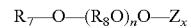

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid mono and di ethanolamide and myristic fatty acid mono and di ethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants useful in the compositions according to invention are $C_{10}$-$C_{22}$-fatty alcohol ethoxylates. Suitable non-limiting examples are oleth-10, oleth-11, oleth-12, oleth-15, oleth-16, oleth-20, oleth-25, oleth-30, oleth-35, oleth-40, laureth-10, laureth-11, laureth-12, laureth-13, laureth-15, laureth-16, laureth-20, laureth-25, laureth-30, laureth-35, laureth-40, laureth-50, ceteth-10, ceteth-12, ceteth-14, ceteth-15, ceteth-16, ceteth-17, ceteth-20, ceteth-25, ceteth-30, ceteth-40, ceteth-45, cetoleth-10, cetoleth-12, cetoleth-14, cetoleth-15, cetoleth-16, cetoleth-17, cetoleth-20, cetoleth-25, cetoleth-30, cetoleth-40, cetoleth-45, ceteareth-10, ceteareth-12, ceteareth-14, ceteareth-15, ceteareth-16, ceteareth-18, ceteareth-20, ceteareth-22, ceteareth-25, ceteareth-30, ceteareth-40, ceteareth-45, ceteareth-50, isosteareth-10, isosteareth-12, isosteareth-15, isosteareth-20, isosteareth-22, isosteareth-25, isosteareth-50, steareth-10, steareth-11, steareth-14, steareth-15, steareth-16, steareth-20, steareth-25, steareth-30, steareth-40, steareth-50, steareth-80 and steareth-100. Additional examples of similar compounds can be found in the cosmetic ingredient dictionaries and cosmetic textbooks.

Further non-ionic surfactants within the meaning of the present invention are polyalkyleneglycol ether of fatty acid glyceride or partial glyceride with at least 30 polyalkylene units are with 30 to 1000, preferably 30 to 500, more preferably 30 to 200 and most preferably 40 to 100 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil, PEG-200 castor oil. Additional examples of similar compounds can be found in the cosmetic ingredient dictionaries and cosmetic textbooks.

Further suitable non-ionic surfactants are monoglycerides such as glyceryl stearate, glyceryl palmitate, glyceryl myristate, glyceryl behenate.

As further surfactant component, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Further, suitable within the meaning of the present invention are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono-, di- or tri alkyl phosphates.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

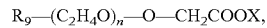

$R_9$—$(C_2H_4O)_n$—O—$CH_2COOX$, wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Concentration of one or more surfactant in the compositions according to present invention is in the range of 0.01 to 5%, preferably 0.05 to 2.5% and more preferably 0.1 to 1% by weight calculated to total composition excluding propellant. Preferred surfactants are non-ionic, amphoteric and cationic ones. The most preferred is non-ionic surfactants.

The composition of the present invention may comprise polyols at a concentration of 0.5 to 15%, preferably 1 to 10%, more preferably 2 to 5% by weight calculated to the total concentration excluding propellant. The most preferred ones are glycerine, propylene glycols, butylene glycol and hexylene glycol.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition excluding propellant. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis". $4^{th}$ Ed.

Compositions of the present invention may contain UV filters either for stabilization of the product colour and/or for protection of hair from environmental influences such as loss of elasticity, loss of hair colour (bleaching effect of sun light). Suitable UV-absorbing substance are Polysilicone-15, 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher.

The suitable amount of the UV-absorber ranges from about 0.01% to 1% by weight, calculated to the total composition excluding propellant. Attention should be paid to the stability and solubility especially when using UV filter as salts, e.g. anionic UV filter salts.

The compositions of the present invention can contain one or more organic solvents within the scope of the invention, Suitable ones are ethanol, propanol, isopropanol, isopentane, n-pentane, n.hexane, dimethoxymethane, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The most preferred organic solvents are ethanol, isopropanol and propanol. Concentration of solvents is in the range of 0 to 80% and preferably 5 to 70%, more preferably 10 to 60% and most preferably 10 to 50% by weight calculated to total composition excluding propellant.

Compositions of the present invention may further comprise polyethyleneglycols Suitable non-limiting examples are PEG-14, PEG-20, PEG-23, PEG-25, PEG-90, PEG-115, PEG-160, PEG-14M, PEG-20M, PEG-23M, PEG-25M, PEG-90M, PEG-115M, PEG-160M, etc. Concentration of the high molecular weight polyethyleneglycol, one or mixture of more than one, is in the range of 0.05% to 2.5%, preferably 0.1% to 1.5% and most preferably between 0.1 to 1.0% by weight calculated to total composition excluding propellant.

In a further embodiment of the present invention, the compositions comprise at least one direct dye for colouring hair. Suitable direct dyes are cationic, anionic, neutral dyes and their mixtures as available commercially from various suppliers and used mainly in semipermanent hair coloration.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable direct dyes are anionic dye. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. When using direct dyes of various categories, their compatibility must be checked.

The above mentioned dyestuffs are also used especially the anionic ones for product colouring at reduced concentrations.

Concentration of direct dyes in the compositions of the present invention is within the range of 0.001 to 5%, preferably 0.01 to 3% and more preferably 0.05 to 2%, and most preferably 0.1 to 1% by weight calculated to total composition, calculated to total composition.

Furthermore compositions of the present invention can comprise all substances customarily found in such preparations. Examples of such substances are complexing agents, preservatives, fragrances, etc.

The following examples are to illustrate the invention but not to limit.

EXAMPLE 1

Hair Spray

|  | % by weight |
|---|---|
| Phenyl trimethicone | 1.50 |
| VP/VA copolymer | 1.00 |
| Isopropyl myristate | 1.50 |
| Dimethicone | 25.00 |

| | % by weight |
|---|---|
| Rice starch *Oryza sativa* | 10.00 |
| Fragrance | q.s. |
| Ethanol | q.s to 100% |

The above composition was prepared by dissolving—dispersing all ingredients one by one in ethanol.

The above composition was filled into an aerosol can with 55% by weight bulk, 40% by weight propane/butane and 5% by weight dimethylether, all values are calculated to total composition.

The hair styled with the above composition is mattified and has excellent volume and body.

EXAMPLE 2

Aerosol Foam

| | % by weight |
|---|---|
| *Oryza Sativa* (Rice) Starch | 5.00 |
| Laureth-4 | 0.30 |
| VP/VA Copolymer | 5.00 |
| PEG-60 hydrogenated castor oil | 0.3 |
| Fragrance | q.s. |
| Water | q.s to 100% |

The above composition was filled into an aerosol can with 90% by weigh bulk and 10% by weight propane butane, all values are calculated to total composition.

EXAMPLE 3

Hair Spray

| | % by weight |
|---|---|
| *Oryza Sativa* (Rice) Starch | 5.00 |
| Acrylates/t-butylacrylamide Copolymer | 5.00 |
| Ethanol | q.s. to 100% |

The above composition was filled into an aerosol can with 55% by weight bulk and 25% by weight n-pentane and 20% fluorinated alkane, all values are calculated to total composition.

EXAMPLE 4

Aerosol Foam

| | % by weight |
|---|---|
| *Oryza Sativa* (Rice) Starch | 5.00 |
| Laureth-4 | 0.30 |
| VP/VA Copolymer | 5.00 |
| PEG-60 hydrogenated castor oil | 0.3 |
| Basic red 51 | 0.1 |
| Fragrance | q.s. |
| Water | q.s to 100% |

The above composition was filled into an aerosol can with 90% by weigh bulk and 10% by weight propane butane, all values are calculated to total composition.

EXAMPLE 5

Aerosol Foam

| | % by weight |
|---|---|
| *Oryza Sativa* (Rice) Starch | 5.00 |
| Laureth-4 | 0.30 |
| VP/VA Copolymer | 5.00 |
| PEG-60 hydrogenated castor oil | 0.3 |
| Basic yellow 87 | 0.1 |
| Basic orange 31 | 0.05 |
| Fragrance | q.s. |
| Water | q.s to 100% |

The above composition was filled into an aerosol can with 90% by weigh bulk and 10% by weight propane butane, all values are calculated to total composition.

EXAMPLE 6

Aerosol Foam

| | % by weight |
|---|---|
| *Oryza Sativa* (Rice) Starch | 5.00 |
| Laureth-4 | 0.30 |
| VP/VA Copolymer | 5.00 |
| PEG-60 hydrogenated castor oil | 0.3 |
| Ethanol | 10.0 |
| Basic yellow 87 | 0.1 |
| Basic orange 31 | 0.05 |
| Fragrance | q.s. |
| Water | q.s to 100% |

The above composition was filled into an aerosol can with 90% by weigh bulk and 10% by weight propane butane, all values are calculated to total composition.

EXAMPLE 7

Aerosol Foam

| | % by weight |
|---|---|
| *Oryza Sativa* (Rice) Starch | 5.00 |
| Laureth-4 | 0.30 |
| VP/VA Copolymer | 5.00 |
| PEG-60 hydrogenated castor oil | 0.3 |
| Ethanol | 10.0 |
| Anionic dye CI 17200 | 0.1 |
| Fragrance | q.s. |
| Water | q.s to 100% |

The above composition was filled into an aerosol can with 90% by weigh bulk and 10% by weight propane butane, all values are calculated to total composition.

The invention claimed is:
1. A process for styling hair, the process comprising:
   applying an aerosol composition onto one hair selected from wet hair and dry hair, wherein the aerosol composition comprises:

an aqueous, aqueous—alcoholic or alcoholic medium;
a natural rice starch present at a concentration of 0.1 to 25% by weight calculated to total composition excluding propellant;
at least one propellant;
one or more film forming polymer, selected from VP/VA copolymer, Acrylates/Octylacrylamide copolymer, Polyquaternium-16, and Acrylates/t-butylacrylamide copolymer, at a concentration of 0.1 to 20% by weight calculated to total composition excluding propellant, and
a polyethyleneglycol ether of fatty acid glyceride or partial glyceride with polyethyleneglycol units in a range from 30 to 1000,
wherein the aerosol composition is an aerosol foam composition; and
styling the one hair without rinsing off the aerosol composition.

2. The process according to claim 1, wherein the propellant is at least one propellant selected from n-butane, i-butane, butane, propane, 1,1 difluoroethane, tetrafluoroethane and dimethylether or mixtures thereof.

3. The process according to claim 1, wherein the aerosol composition further comprises at least one synthetic or natural oil present at a concentration of 0.1 to 40% by weight, calculated to total concentration excluding propellant.

4. The process according to claim 1, wherein the aerosol composition further comprises at least one wax present at a concentration of 0.01 to 20% by weight, calculated to total concentration excluding propellant.

5. The process according to claim 1, wherein the aerosol composition further comprises an organic solvent.

6. The process according to claim 1, wherein the aerosol composition further comprises at least one surfactant selected from anionic surfactants, cationic surfactants, nonionic surfactants and amphoteric surfactants.

7. The process according to claim 1, wherein the aerosol composition further comprises at least one UV filter.

8. The process according to claim 1, wherein the aerosol composition further comprises at least one direct dye.

9. The process according to claim 1, wherein the one or more film-forming polymer is present at a concentration of between 2 to 10 wt. %, calculated to the total composition excluding propellant.

10. The process according to claim 1, wherein the polyethyleneglycol ether of fatty acid glyceride or partial glyceride is selected from the group consisting of PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-50 castor oil, PEG-55 castor oil, PEG-60 castor oil, PEG-80 castor oil, PEG-100 castor oil and PEG-200 castor oil.

11. The process according to claim 10, wherein the polyethyleneglycol ether of fatty acid glyceride or partial glyceride is present at a concentration from 0.01 to 5 wt. %, calculated to the total composition excluding propellant.

12. The process according to claim 11, wherein the polyethyleneglycol ether of fatty acid glyceride or partial glyceride is PEG-60 hydrogenated castor oil.

13. The process according to claim 10, wherein the polyethyleneglycol ether of fatty acid glyceride or partial glyceride is present at a concentration from 0.1 to 1 wt. %, calculated to the total composition excluding propellant.

14. The process according to claim 1, further comprising:
restyling the styled hair, with or without wetting, to give the styled hair a new style.

* * * * *